(12) United States Patent
Eller

(10) Patent No.: US 7,651,523 B2
(45) Date of Patent: Jan. 26, 2010

(54) INTRALUMINAL DEVICE WITH FLEXIBLE REGIONS

(75) Inventor: Alan A. Eller, Plainfield, IN (US)

(73) Assignee: Cook Incorporated, Bloomington, IN (US)

( * ) Notice: Subject to any disclaimer, the term of this patent is extended or adjusted under 35 U.S.C. 154(b) by 253 days.

(21) Appl. No.: 11/779,014

(22) Filed: Jul. 17, 2007

(65) Prior Publication Data

US 2008/0021539 A1 Jan. 24, 2008

Related U.S. Application Data

(60) Provisional application No. 60/833,181, filed on Jul. 24, 2006.

(51) Int. Cl.
*A61F 2/06* (2006.01)
(52) U.S. Cl. .................................................. 623/1.15
(58) Field of Classification Search ........ 623/1.11–1.49
See application file for complete search history.

(56) References Cited

U.S. PATENT DOCUMENTS

| | | | |
|---|---|---|---|
| 5,104,404 A | 4/1992 | Wolff | 623/1 |
| 5,282,824 A | 2/1994 | Gianturco | 606/198 |
| 5,383,892 A | 1/1995 | Cardon et al. | 606/198 |
| 5,443,496 A | 8/1995 | Schwartz et al. | 623/1 |
| 5,935,161 A * | 8/1999 | Robinson et al. | 128/898 |
| 6,042,606 A * | 3/2000 | Frantzen | 623/1.18 |
| 6,120,534 A | 9/2000 | Ruiz | 623/1.19 |
| 6,187,036 B1 * | 2/2001 | Shaolian et al. | 623/1.15 |
| 6,238,409 B1 | 5/2001 | Hojeibane | 606/194 |
| 6,258,117 B1 | 7/2001 | Camrud et al. | 623/1.16 |
| 6,264,687 B1 | 7/2001 | Tomonto | 623/1.16 |
| 6,325,825 B1 * | 12/2001 | Kula et al. | 623/1.3 |
| 6,485,510 B1 | 11/2002 | Camrud et al. | 623/1.16 |
| 6,547,818 B1 * | 4/2003 | Rourke et al. | 623/1.16 |
| 7,014,654 B2 * | 3/2006 | Welsh et al. | 623/1.15 |
| 7,122,059 B2 * | 10/2006 | Rourke et al. | 623/1.15 |
| 7,135,038 B1 * | 11/2006 | Limon | 623/1.15 |
| 2008/0132994 A1 * | 6/2008 | Burgermeister et al. | 623/1.15 |

\* cited by examiner

*Primary Examiner*—Suzette J Gherbi
(74) *Attorney, Agent, or Firm*—Brinks Hofer Gilson & Lione

(57) ABSTRACT

An intraluminal device is provided with a structural member having an abluminal surface to engage a vessel wall and a luminal surface. The structural member is formed with regions having different thicknesses between the abluminal surface and luminal surface. The intraluminal device may be useful where improved axial flexibility is desired.

17 Claims, 2 Drawing Sheets

INTRALUMINAL DEVICE WITH FLEXIBLE REGIONS

This application claims priority to U.S. Provisional Application No. 60/833,181, filed Jul. 24, 2006, which is hereby incorporated by reference herein.

BACKGROUND

The present invention relates generally to medical devices and more particularly to intraluminal devices.

Stents have become relatively common devices for treating a number of organs, such as the vascular system, colon, biliary tract, urinary tract, esophagus, trachea and the like. Stents are useful in a variety of medical procedures and are often used to treat various types of aneurysms. Stents are also useful in treating other ailments including blockages, occlusions, narrowing ailments and other related problems that restrict flow through a passageway (generally referred to as a stenosis).

For example, stents may be used to treat numerous vessels in the vascular system, including coronary arteries, peripheral arteries (e.g., carotid, brachial, renal, iliac and femoral), and other vessels. Stents have become a popular alternative for treating vascular conditions because stenting procedures are considerably less invasive than other alternatives. As an example, stenoses in the coronary arteries has traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that is risky and requires a long recovery time for the patient. By contrast, stenting procedures are performed transluminally and do not require open surgery. Thus, recovery time is reduced and the risks of surgery are minimized.

Many different types of stents and stenting procedures are possible. In general, however, stents are typically designed as tubular support structures that may be inserted percutaneously and transluminally through a body passageway. Typically, stents are made from a structure that wraps around at least a portion of a circumference and are adapted to compress and expand between a smaller and larger diameter. However, other types of stents are designed to have a fixed diameter and are not generally compressible. Although stents may be made from many types of materials, including non-metallic materials and natural tissues, common examples of metallic materials that may be used to make stents include stainless steel, nitinol, cobalt-chrome alloys, amorphous metals, tantalum, platinum, gold and titanium. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing to keep the passageway open to facilitate fluid flow through the passageway. Stents may also be used to support a graft layer. However, these are only some of the examples of how stents may be used, and stents may be used for other purposes as well.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient might die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

Particular stent designs and implantation procedures vary widely. For example, stents are often generally characterized as either balloon-expandable or self-expandable. However, the uses for balloon-expandable and self-expandable stents frequently overlap and procedures related to one type of stent are frequently adapted to other types of stents.

Balloon-expandable stents are frequently used to treat stenosis of the coronary arteries. Usually, balloon-expandable stents are made from ductile materials that plastically deform relatively easily. In the case of stents made from metal, 316L stainless steel which has been annealed is a common choice for this type of stent. One procedure for implanting balloon-expandable stents involves mounting the stent circumferentially on the balloon of a balloon-tipped catheter and threading the catheter through a vessel passageway to the area to be treated. Once the balloon is positioned at the narrowed portion of the vessel to be treated, the balloon is expanded by pumping saline through the catheter to the balloon. The balloon then simultaneously dilates the vessel and radially expands the stent within the dilated portion. The balloon is then deflated and the balloon-tipped catheter is retracted from the passageway. This leaves the expanded stent permanently implanted at the desired location. Ductile metal lends itself to this type of stent since the stent may be compressed by plastic deformation to a small diameter when mounted onto the balloon. When the balloon is later expanded in the vessel, the stent once again plastically deforms to a larger diameter to provide the desired radial support structure. Traditionally, balloon-expandable stents have been more commonly used in coronary vessels than in peripheral vessels because of the deformable nature of these stents. One reason for this is that peripheral vessels tend to experience frequent traumas from external sources (e.g., impacts to a person's arms, legs, etc.) which are transmitted through the body's tissues to the vessel. In the case of peripheral vessels, there is an increased risk that an external trauma could cause a balloon-expandable stent to once again plastically deform in unexpected ways with potentially severe and/or catastrophic results. In the case of coronary vessels, however, this risk is minimal since coronary vessels rarely experience traumas transmitted from external sources. In addition, one advantage of balloon-expandable stents is that the expanded diameter of the stent may be precisely controlled during implantation. This is possible because the pressure applied to the balloon may be controlled by the physician to produce a precise amount of radial expansion and plastic deformation of the stent.

Self-expandable stents are increasingly being used by physicians because of their adaptability to a variety of different conditions and procedures. Self-expandable stents are usually made of shape memory materials or other elastic materials that act like a spring. Typical metals used in this type of stent include nitinol and 304 stainless steel. However, other materials may also be used. To facilitate stent implantation, self-expandable stents are normally installed on the end of a catheter in a low profile, compressed state. The stent is typically retained in the compressed state by inserting the stent into a sheath at the end of the catheter. The stent is then guided to the portion of the vessel to be treated. Once the catheter and stent are positioned adjacent the portion to be treated, the stent is released by pulling, or withdrawing, the sheath rearward. Normally, a step or other feature is provided on the catheter to prevent the stent from moving rearward with the sheath. After the stent is released from the retaining sheath, the stent radially springs outward to an expanded diameter until the stent contacts and presses against the vessel wall. Traditionally, self-expandable stents have been used in a number of peripheral arteries in the vascular system due to the shape memory characteristic of these stents. One advantage of self-expandable stents for peripheral arteries is that traumas from external sources do not permanently deform the stent. As a result, the stent may temporarily deform during unusually harsh traumas and spring back to its expanded state once the trauma is relieved. However, self-expandable stents may be used in many other applications as well.

The above-described examples are only some of the applications in which stents are used by physicians. Many other applications for stents are known and/or may be developed in the future.

SUMMARY

An intraluminal device is described. The intraluminal device may be a stent-graft or a stent or other intraluminal device. A structural member of the device has an abluminal surface to engage the wall of a body vessel. The structural member also has a luminal surface that faces toward the inner lumen of the body vessel. The structural member may include regions that are thinner and thicker relative to each other between the abluminal and luminal surfaces. This may improve axial flexibility of stents and stent-grafts. Additional details and advantages are described below in the detailed description.

The invention may include any of the following aspects in various combinations and may also include any other aspect described below in the written description or in the attached drawings.

A intraluminal device, comprising:

a structural member adapted to engage a wall of a body lumen, the structural member comprising a length comprising an abluminal surface facing radially outward and a luminal surface facing radially inward;

a first region of the structural member along the length comprising a first thickness between the abluminal surface and the luminal surface;

a second region of the structural member along the length adjacent the first region comprising a second thickness between the abluminal surface and the luminal surface, the second region being disposed proximal to the first region; and a third region of the structural member along the length adjacent the second region comprising a third thickness between the abluminal surface and the luminal surface, the third region being disposed proximal to the second region;

wherein the second region is disposed between the first region and the third region and the second thickness is thinner than the first thickness and the third thickness.

The intraluminal device, wherein the structural member forms a portion of a stent, the structural member wrapping around a circumference of the stent, the length of the structural member being angled relative to a longitudinal axis of the stent.

The intraluminal device, further comprising a graft layer attached to the stent.

The intraluminal device, wherein the structural member comprises a first ring structure, and further comprising a second ring structure separated from the first ring structure, the first ring structure and the second ring structure each being attached to the graft layer.

The intraluminal device, wherein the first ring structure is disposed at a distal end of the stent.

The intraluminal device, wherein the second ring structure is disposed proximal from the first ring segment, the second ring structure having a substantially uniform thickness.

The intraluminal device, wherein the structural member is disposed at a distal end of the intraluminal device.

The intraluminal device, wherein the structural member is a wire.

The intraluminal device, wherein first region smoothly transitions to the second region and the second region smoothly transitions to the third region, the first region, the second region and the third region comprising curved surfaces.

The intraluminal device, wherein the second region is thinner than the first region and the third region across a transverse direction to the abluminal surface and the luminal surface.

The intraluminal device, further comprising a fourth region of the structural member along the length adjacent the third region comprising a fourth thickness between the abluminal surface and the luminal surface, the fourth region being disposed proximal to the third region; and a fifth region of the structural member along the length adjacent the fourth region comprising a fifth thickness between the abluminal surface and the luminal surface, the fifth region being disposed proximal to the fourth region;

wherein the fourth region is disposed between the third region and the fifth region and the fourth thickness is thinner than the third thickness and the fifth thickness.

The intraluminal device, further comprising a sixth region of the structural member along the length adjacent the fifth region comprising a sixth thickness between the abluminal surface and the luminal surface, the sixth region being disposed proximal to the fifth region; and a seventh region of the structural member along the length adjacent the sixth region comprising a seventh thickness between the abluminal surface and the luminal surface, the seventh region being disposed proximal to the sixth region;

wherein the sixth region is disposed between the fifth region and the seventh region and the sixth thickness is thinner than the fifth thickness and the seventh thickness.

The intraluminal device, further comprising a eighth region of the structural member along the length adjacent the seventh region comprising a eighth thickness between the abluminal surface and the luminal surface, the eighth region being disposed proximal to the seventh region; and a ninth region of the structural member along the length adjacent the eighth region comprising a ninth thickness between the abluminal surface and the luminal surface, the ninth region being disposed proximal to the eighth region;

wherein the eighth region is disposed between the seventh region and the ninth region and the eighth thickness is thinner than the seventh thickness and the ninth thickness.

The intraluminal device, wherein the structural member comprises a first bend in one direction at one end of the length and a second bend in an opposite direction at another end of the length, a thickness of the first bend and the second bend between the abluminal surface and the luminal surface being substantially the same as the first thickness.

The intraluminal device, wherein the structural member forms a portion of a stent, the structural member being a wire, and first region smoothly transitions to the second region and the second region smoothly transitions to the third region, the first region, the second region and the third region comprising curved surfaces, the structural member comprising a first bend in one direction at one end of the length and a second bend in an opposite direction at another end of the length, a thickness of the first bend and the second bend between the abluminal surface and the luminal surface being substantially the same as the first thickness, and wherein the structural member wraps around a circumference of the stent, the length of the structural member being angled relative to a longitudinal axis of the stent and a plane transverse to the stent.

The intraluminal device, wherein the structural member is disposed at a distal end of the stent, and further comprising a fourth region of the structural member along the length adjacent the third region comprising a fourth thickness between the abluminal surface and the luminal surface, the fourth region being disposed proximal to the third region; and a fifth region of the structural member along the length adjacent the fourth region comprising a fifth thickness between the abluminal surface and the luminal surface, the fifth region being disposed proximal to the fourth region;

wherein the fourth region is disposed between the third region and the fifth region and the fourth thickness is thinner than the third thickness and the fifth thickness.

The intraluminal device, further comprising a sixth region of the structural member along the length adjacent the fifth region comprising a sixth thickness between the abluminal surface and the luminal surface, the sixth region being disposed proximal to the fifth region; and a seventh region of the structural member along the length adjacent the sixth region comprising a seventh thickness between the abluminal surface and the luminal surface, the seventh region being disposed proximal to the sixth region; and wherein the sixth region is disposed between the fifth region and the seventh region and the sixth thickness is thinner than the fifth thickness and the seventh thickness, and the second region, the fourth region and the sixth region are thinner than the first region, the third region, the fifth region and the seventh region across a transverse direction to the abluminal surface and the luminal surface.

The intraluminal device, further comprising a graft layer attached to the stent, the structural member comprising a first ring structure, and further comprising a second ring structure separated from the first ring structure, the first ring structure and the second ring structure each being attached to the graft layer, wherein the second ring structure is disposed proximal from the first ring segment, the second ring structure having a substantially uniform thickness.

A stent, comprising:

a plurality of ring structures extending around a circumference of the stent, the ring structures comprising a plurality of angular struts interconnected by a series of bends, wherein the angular struts comprise at least one thicker region disposed between two thinner regions, the thicker region being thicker than the thinner regions along a first length between an abluminal surface of the stent and a luminal surface of the stent and also being thicker along a second length transverse to the first length.

A stent-graft, comprising:

a plurality of ring structures extending around a circumference of the stent-graft, each of the ring structures being formed from a wire and comprising a plurality of angular struts interconnected by a series of bends, the plurality of ring structures being attached to a graft;

wherein a distal most ring structure comprises at least three thinner regions along each of the angular struts interposed by two thicker regions, the thinner regions being defined by smaller diameter cross-sections than the thicker regions; and at least one of the ring structures disposed proximal from the distal most ring structure comprising a substantially uniform cross-section around the circumference of the stent-graft.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
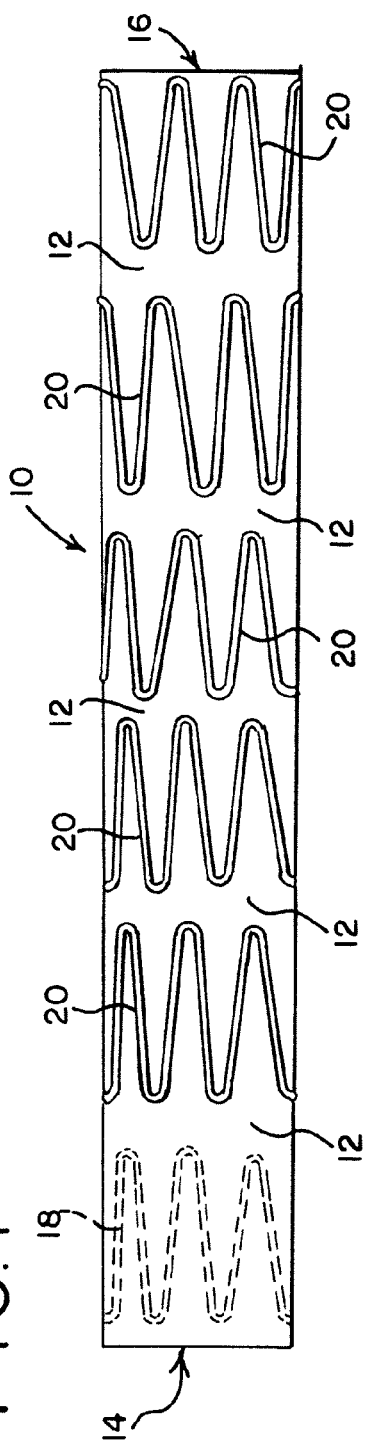
FIG. 1 is a side elevational view of a stent-graft.
Figure 2:
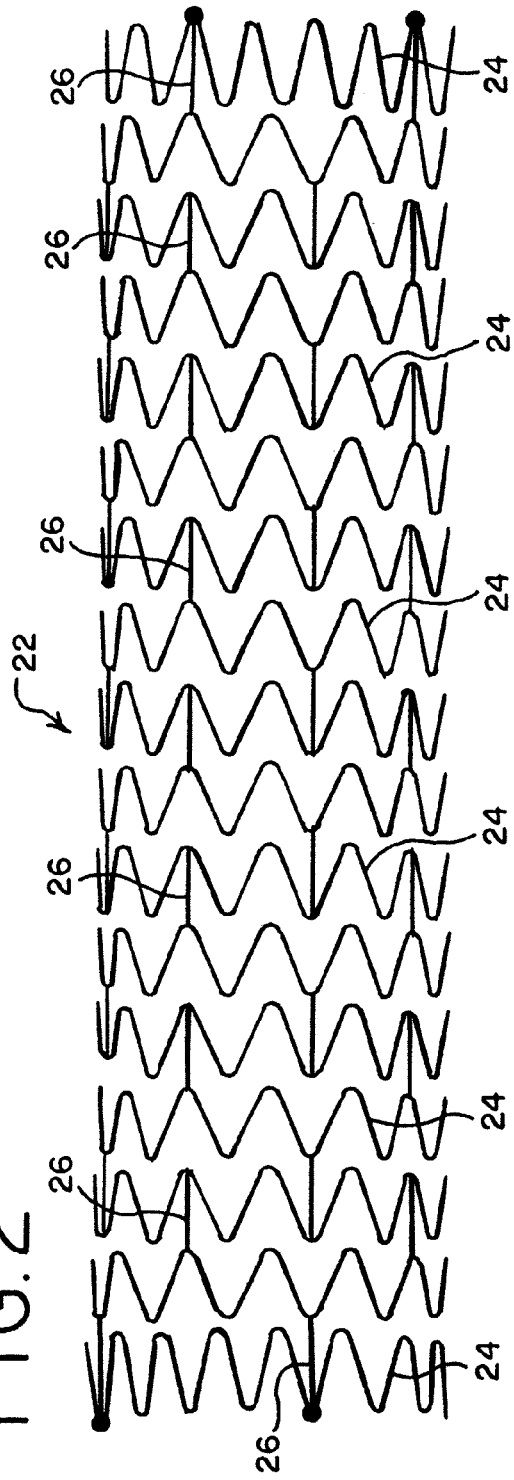
FIG. 2 is a side elevational view of a bare stent.

Referring now to the drawings, a stent-graft 10 is shown in FIG. 1 and a bare stent 22 is shown in FIG. 2. Numerous types of stents and other intraluminal devices are known in the art and the illustrated stents are only a few of the examples where the invention may be used.

In FIG. 1, a stent-graft 10 is shown. Stent-grafts are typically used to treat vascular aneurysms but may have other uses as well. The stent-graft 10 includes a graft layer 12 extending from the distal end 14 of the stent-graft 10 to the proximal end 16 of the stent-graft 10. Various types of graft materials are known, such as ePTFE, silicone and Dacron. However, other types of conventional graft layers may be used. A series of separate stents 18, 20 (or ring structures 18, 20) are attached to the stent-graft 10 to provide structural support to the graft layer 12. Preferably, the stents 18, 20 are made from a wire may be made from other structures as well. The graft layer 12 may be attached to the stents 18, 20 in a variety of ways, such as with sutures, adhesives, melting and other known techniques. As shown, it is preferable to attach the stent 18 at the distal end 14 of the stent-graft 10 to the inside of the graft layer 12. This provides a seal between the graft layer 12 and the vessel wall when the stent-graft 10 is implanted to prevent blood from flowing between the outer surface of the graft layer 12 and the vessel wall. The remaining stents 20 may be attached to the outside of the graft layer 12 to provide a smooth surface on the inside of the graft layer 12 for blood flow through the stent-graft 10.

In FIG. 2, a bare stent 22 is shown. Bare stents 22 are often used to treat vascular stenoses but are also used for other treatments as well. The stent 22 shown in FIG. 2 is configured with a series of ring structures 24 that are interconnected with longitudinal segments 26. Preferably, the stent 22 is made by laser cutting the stent structure 22 from a cannula. The stents 10, 22 shown in FIGS. 1 and 2 may be either self-expandable or balloon expandable. The stents 10, 22 may also be made from metals, such as stainless steel or nitinol, or may be made from other materials.

Figure 3:
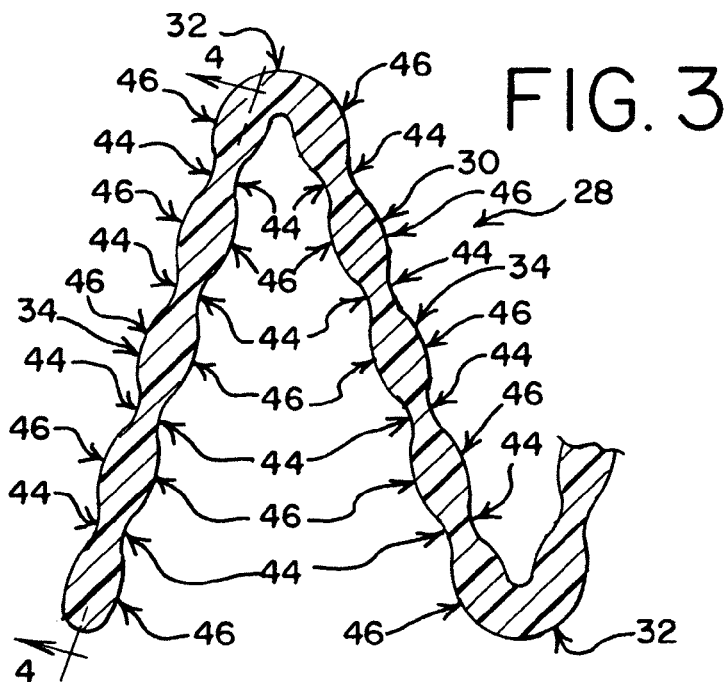
FIG. 3 is a side elevational view of a portion of a stent.
Figure 4:
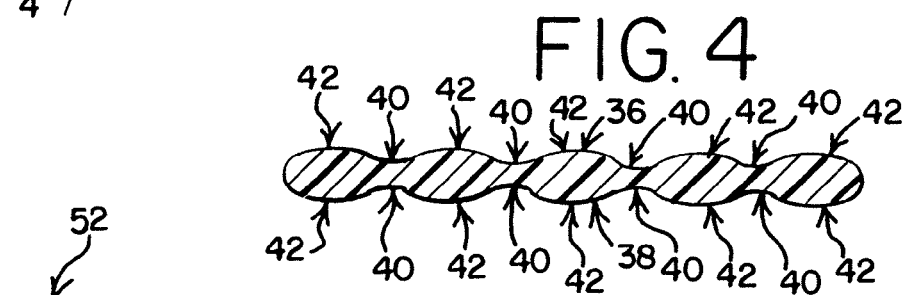
FIG. 4 is a cross-sectional view of the stent along line 44 of FIG. 3.

Turning to FIG. 3, a portion of a stent 28 is shown. The structural member 30 shown in FIG. 3 is formed with a series of opposing bends 32 and angular lengths 34 between each pair of bends 32. As shown in FIGS. 1 and 2, it is preferred to have the structural member 30 wrap around the circumference of the stent 28 to form a ring structure 18, 20, 24. In FIG. 4, a cross-section is shown of the structural member 30 along section line 4-4 from FIG. 3. As shown, the structural member 30 has an abluminal surface 36 that faces radially outward and a luminal surface 38 that faces radially inward. Thus, the abluminal surface 36 is adapted to face toward a vessel wall, and the luminal surface 38 is adapted to face toward the lumen of a vessel.

Figure 5:
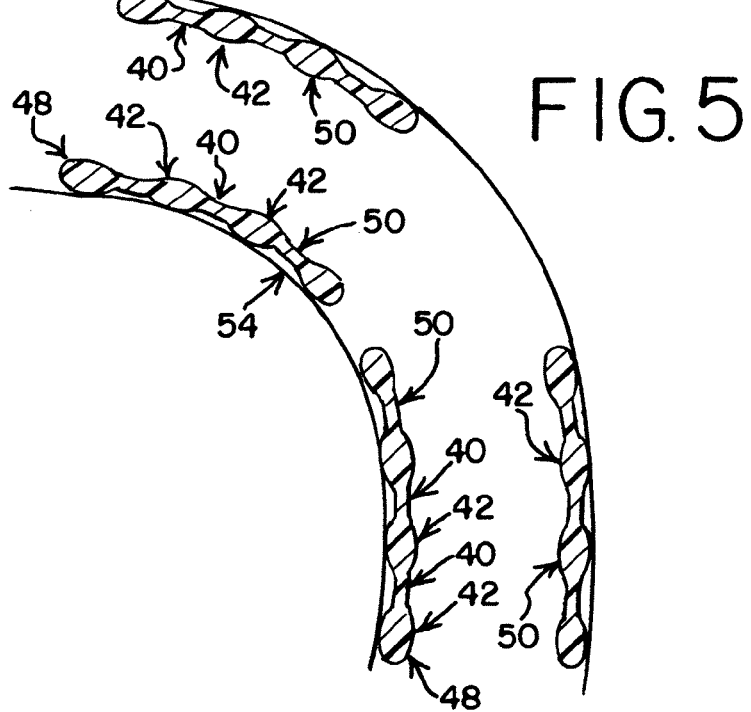
FIG. 5 is a side view of a stent implanted in a body vessel.

Along the length of the structural member 30, the thickness of the structural member 30 between the abluminal surface 36 and the luminal surface 38 varies. As shown, the structural member 30 may have thinner regions 40 positioned between thicker regions 42. Any number of thinner and thicker regions 40, 42 may be used as desired. For example, in FIGS. 3 and 4, four thinner regions 40 are positioned alternately between five thicker regions 42. As shown in FIG. 5, three thinner regions 40 are positioned alternately between four thicker regions 42. Other arrangements of thinner and thicker regions 40, 42 are also possible. Preferably, the thinner regions 40 and the thicker regions 42 transition smoothly from one region to the next without abrupt transitions. Smooth transitions with curved surfaces as shown are preferable to avoid stress concentrations during use, which may reduce fatigue life. In addition, the bends 32 in the structural member 30 preferably have a thickness that is substantially the same as the thicker regions 42.

The thinner and thicker regions 40, 42 may be formed into the structural member 30 in a variety of ways. Preferably, the structural member 30 is made from a wire. If the structural member 30 is made from a wire, the thinner and thicker regions 40 42 may be formed into the wire simultaneously with the forming of the wire. For example, a variable diameter extruder may be used. In addition, the thinner and thicker regions 40, 42 may be formed into a wire after a uniform diameter wire is extruded by machining the wire (e.g., grinding) or by forging the wire. The thinner and thicker regions 40, 42 may also be formed into a wire by casting the wire. Preferably, the thinner and thicker regions 40, 42 are formed into the wire before the wire is formed into a ring structure 18, 20 with bends 32 as shown in FIG. 1. If a wire is used for the structural member 30, the thinner and thicker regions 40, 42 may be formed as diameter changes in the wire, where the thinner regions 40 correspond to small diameter regions of the wire and the thicker regions 42 correspond to larger diameter regions of the wire. Thus, as shown in FIGS. 3 and 4, the thinner and thicker regions 40, 42 of the wire between the abluminal and luminal surfaces 36, 38 may be substantially the same as corresponding thinner and thicker width regions 44, 46 transverse to the abluminal and luminal surfaces 36, 38. Accordingly, the thinner thickness regions 40 may also have thinner width regions 44 than the thicker width regions 46. However, the thinner and thicker thickness regions 40, 42 may be formed into a wire without having corresponding thinner and thicker width regions 44, 46. For example, the width of the wire may be substantially constant, or the width of the wire may be wider at the thinner thickness regions 40.

The thinner and thicker regions 40, 42 may also be formed into a structural member 24, 26 that is laser cut from a cannula as shown in FIG. 2. Preferably, the thinner and thicker regions 40, 42 are formed into the cannula before the structural members 24, 26 are cut from the cannula. The thinner and thicker regions 40, 42 may be formed into the cannula using the same techniques described above.

One of the advantages of the described stents is that the stent may conform better to the shape of curved body lumens. This may be particularly useful in stenting procedures involving the aortic arch, but may also be useful in many other treatments as well. One problem that may occur with stents having structural members formed from a uniform diameter or thickness is that portions of the structural members may not contact the vessel wall due to the tendency of the structural members to remain straight. This is sometimes referred to as a fish scaling effect. In general, this may occur along a curved portion of a vessel where a straight length of a structural member lies tangential to a portion of a curve instead of bending with the curvature of the vessel wall. The curvature of the vessel wall may also be thought of as a hinge point that contacts a portion of the structural member, with either a distal or proximal portion of the structural member being angled away from the remaining vessel curvature.

Structural members that do not conform to vessel curvatures may be undesirable for several reasons. For example, when a stent is used to support a dilated stenosis, the stent may not provide complete support in areas in which the stent is not in full contact with the vessel wall. In addition, portions of the structural members may extend into the vessel lumen instead of lying flat against the vessel wall and may increase turbulence in the blood flow through the lumen. Where a stent-graft is used to treat an aneurysm, a structural member that does not fully conform to the vessel wall may also allow small amounts of blood to pass between the graft layer and the vessel wall.

As shown in FIG. 5, one advantage of the described stents is that the structural members 50 may conform to a vessel wall better than conventional stents. As shown in FIG. 5, a stent 48 is implanted in a body vessel 52 along a curved portion 54 of the vessel 52. The stent 48 shown in FIG. 5 is only one example of various medical devices that may be used. For example, the stent 48 may be either a stent-graft 10 or a bare stent 22 as shown in FIGS. 1 and 2. The stent 48 may also be self-expandable or balloon expandable. Other intraluminal medical devices are also possible, such as blood filters. As shown in FIG. 5, the stent 48 bends axially along the curvature 54 of the vessel 52. Thus, unlike some conventional stents, the straight lengths of the structural members 50 conform to the shape of the vessel wall 52 instead of extending in a generally straight axial direction. This axial flexibility is facilitated by the thinner and thicker regions 40, 42 of the structural members 50, which allows the structural members 50 to flex in the axial direction. The thinner and thicker regions 40, 42 may also be combined with portions without thinner and thicker regions 40, 42 as desired. For example, in a stent-graft 10 as shown in FIG. 1, the ring structure 18 at the distal end 14 of the stent-graft 10 may incorporate thinner and thicker regions 40, 42 as described herein to improve sealing of the graft layer 12 against a vessel wall. However, the remaining ring structures 20 could be made from constant diameter wires as desired.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. Intraluminal device, comprising:
   a structural member adapted to engage a wall of a body lumen, said structural member comprising a length comprising an abluminal surface facing radially outward and a luminal surface facing radially inward;
   a first region of said structural member along said length comprising a first thickness between said abluminal surface and said luminal surface;
   a second region of said structural member along said length adjacent said first region comprising a second thickness between said abluminal surface and said luminal surface, said second region being disposed proximal to said first region;
   a third region of said structural member along said length adjacent said second region comprising a third thickness between said abluminal surface and said luminal surface, said third region being disposed proximal to said second region;
   wherein said second region is disposed between said first region and said third region and said second thickness is thinner than said first thickness and said third thickness;
   a fourth region of said structural member along said length adjacent said third region comprising a fourth thickness between said abluminal surface and said luminal surface, said fourth region being disposed proximal to said third region;
   a fifth region of said structural member along said length adjacent said fourth region comprising a fifth thickness between said abluminal surface and said luminal surface, said fifth region being disposed proximal to said fourth region,
   wherein said fourth region is disposed between said third region and said fifth region and said fourth thickness is thinner than said third thickness and said fifth thickness;
   a sixth region of said structural member along said length adjacent said fifth region comprising a sixth thickness between said abluminal surface and said luminal surface, said sixth region being disposed proximal to said fifth region;
   a seventh region of said structural member along said length adjacent said sixth region comprising a seventh thickness between said abluminal surface and said luminal surface, said seventh region being disposed proximal to said sixth region,
   wherein said sixth region is disposed between said fifth region and said seventh region and said sixth thickness is thinner than said fifth thickness and said seventh thickness;
   an eighth region of said structural member along said length adjacent said seventh region comprising an eighth thickness between said abluminal surface and said luminal surface, said eighth region being disposed proximal to said seventh region; and
   a ninth region of said structural member along said length adjacent said eighth region comprising a ninth thickness between said abluminal surface and said luminal surface, said ninth region being disposed proximal to said eighth region;
   wherein said eighth region is disposed between said seventh region and said ninth region and said eighth thickness is thinner than said seventh thickness and said ninth thickness.

2. The intraluminal device according to claim 1, said structural member forms a portion of a stent, said structural member wrapping around a circumference of said stent, said length of said structural member being angled relative to a longitudinal axis of said stent.

3. The intraluminal device according to claim 2, further comprising a graft layer attached to said stent.

4. The intraluminal device according to claim 3, wherein said structural member comprises a first ring structure, and further comprising a second ring structure separated from said first ring structure, said first ring structure and said second ring structure each being attached to said graft layer.

5. The intraluminal device according to claim 4, wherein said first ring structure is disposed at a distal end of said stent.

6. The intraluminal device according to claim 5, wherein said second ring structure is disposed proximal from said first ring segment, said second ring structure having a substantially uniform thickness.

7. The intraluminal device according to claim 1, wherein said structural member is disposed at a distal end of said intraluminal device.

8. The intraluminal device according to claim 1, wherein said structural member is a wire.

9. The intraluminal device according to claim 1, wherein first region smoothly transitions to said second region and said second region smoothly transitions to said third region, said first region, said second region and said third region comprising curved surfaces.

10. The intraluminal device according to claim 1, wherein said second region is thinner than said first region and said third region across a transverse direction to said abluminal surface and said luminal surface.

11. The intraluminal device according to claim 1, wherein said structural member comprises a first bend in one direction at one end of said length and a second bend in an opposite direction at another end of said length, a thickness of said first bend and said second bend between said abluminal surface and said luminal surface being substantially the same as said first thickness.

12. The intraluminal device according to claim 1, wherein said structural member forms a portion of a stent, said structural member being a wire, and first region smoothly transitions to said second region and said second region smoothly transitions to said third region, said first region, said second region and said third region comprising curved surfaces, said structural member comprising a first bend in one direction at one end of said length and a second bend in an opposite direction at another end of said length, a thickness of said first bend and said second bend between said abluminal surface and said luminal surface being substantially the same as said first thickness, and wherein said structural member wraps around a circumference of said stent, said length of said structural member being angled relative to a longitudinal axis of said stent and a plane transverse to said stent.

13. The intraluminal device according to claim 12, wherein said sixth thickness is thinner than said fifth thickness and said seventh thickness, and said second region, said fourth region and said sixth region are thinner than said first region, said third region, said fifth region and said seventh region across a transverse direction to said abluminal surface and said luminal surface.

14. The intraluminal device according to claim 13, further comprising a graft layer attached to said stent, said structural member comprising a first ring structure, and further comprising a second ring structure separated from said first ring structure, said first ring structure and said second ring structure each being attached to said graft layer, wherein said second ring structure is disposed proximal from said first ring segment, said second ring structure having a substantially uniform thickness.

15. A stent, comprising:
a plurality of ring structures extending around a circumference of said stent, said ring structures comprising a plurality of angular struts interconnected by a series of bends in an undulating configuration whereby said ring structures are expandable from a compressed configuration in which said angular struts are substantially parallel to each other, to an expanded configuration in which said angular struts are angled away from each other about said bends;
wherein said angular struts comprise at least two radially thinner regions disposed between at least three radially thicker regions, one of the at least three radially thicker regions being disposed between said two radially thinner regions, said radially thinner regions having a first radial thickness and said radially thicker regions having a second radial thickness, wherein said second radial thickness of said radially thicker regions is substantially the same as a radial thickness of said bends, and said first thickness of said radially thinner regions is thinner in a radial direction than said thickness of said bends and said at least three radially thicker regions along a first length of said angular struts between an abluminal surface of said stent and a luminal surface of said stent,
wherein, when said stent is implanted in a body lumen, said radially thicker regions flex in at least a radial direction about said radially thinner regions such that said angular struts substantially conform to a shape of a wall of said body lumen along said first length.

16. A stent-graft, comprising:
a plurality of ring structures extending around a circumference of said stent-graft, each of said ring structures being formed from a wire and comprising a plurality of angular struts interconnected by a series of bends in an undulating configuration whereby said ring structures are expandable from a compressed configuration in which said angular struts are substantially parallel to each other, to an expanded configuration in which said angular struts are angled away from each other about said bends, said plurality of ring structures being attached to a graft;
wherein a distal most ring structure comprises at least three radially thinner regions along each of said angular struts interposed by at least two radially thicker regions, said radially thinner regions being defined by smaller diameter cross-sections than said radially thicker regions, and wherein said radially thicker regions have substantially the same radial thickness as said bends; and
at least one of said ring structures disposed proximal from said distal most ring structure comprising a substantially uniform cross-section around said circumference of said stent-graft,
wherein, when said stent-graft is implanted in a body lumen, said radially thicker regions flex in at least a radial direction about said radially thinner regions such that said angular struts substantially conform to a shape of a wall of said body lumen along a length thereof.

17. The stent of claim 15, wherein said at least two radially thinner regions are thinner than said radially thicker region along a second length transverse to said first length.

* * * * *